United States Patent [19]
Schätzle et al.

[11] Patent Number: 5,928,169
[45] Date of Patent: Jul. 27, 1999

[54] APPARATUS FOR TREATING A SUBJECT WITH FOCUSED ULTRASOUND WAVES

[75] Inventors: Ulrich Schätzle, Röttenbach; Erhard Schmidt, Erlangen, both of Germany

[73] Assignee: Siemens Aktiengesellschaft, Munich, Germany

[21] Appl. No.: 08/913,542

[22] PCT Filed: Dec. 15, 1995

[86] PCT No.: PCT/DE95/01805

§ 371 Date: Jun. 20, 1997

§ 102(e) Date: Jun. 20, 1997

[87] PCT Pub. No.: WO96/20471

PCT Pub. Date: Jul. 4, 1996

[30] Foreign Application Priority Data

Dec. 23, 1994 [DE] Germany ............................. 44 46 429

[51] Int. Cl.⁶ ................................................. A61B 17/22
[52] U.S. Cl. ...................... 601/2; 601/3; 601/4; 600/439
[58] Field of Search .............................. 601/2–4; 600/439

[56] References Cited

U.S. PATENT DOCUMENTS

| | | |
|---|---|---|
| 4,159,462 | 6/1979 | Rocha et al. . |
| 4,559,642 | 12/1985 | Miyaji et al. . |
| 5,065,741 | 11/1991 | Uchiyama et al. . |
| 5,158,071 | 10/1992 | Umemura et al. . |
| 5,207,214 | 5/1993 | Romano ...................................... 601/4 |
| 5,387,180 | 2/1995 | Lehmer ....................................... 601/2 |
| 5,445,156 | 8/1995 | Daft et al. ................................ 600/454 |
| 5,524,625 | 6/1996 | Okazaki et al. ......................... 600/439 |
| 5,526,815 | 6/1996 | Granz et al. . |
| 5,665,054 | 9/1997 | Dory ........................................... 601/3 |
| 5,738,635 | 4/1998 | Chapelon et al. ........................... 601/2 |

FOREIGN PATENT DOCUMENTS

| | | |
|---|---|---|
| 0 104 928 | 4/1984 | European Pat. Off. . |
| OS 30 48 527 | 7/1982 | Germany . |
| OS 32 36 218 | 4/1984 | Germany . |

*Primary Examiner*—Brian L. Casler
*Attorney, Agent, or Firm*—Hill & Simpson

[57] ABSTRACT

An apparatus for treating a subject with focused ultrasound waves has an ultrasound transducer composed of a number of ultrasound transducer elements. Each ultrasound transducer element has a memory connected thereto in which, during operation, a bit pattern corresponding to a desired position of the focus of the ultrasound waves is stored. A control unit cyclically addresses the individual memories in parallel such that electrical signals offset in time relative to one another according to the desired position of the focus are present at the respective data outputs of the memories, and these signals are supplied to the respective ultrasound transducer elements connected to the data outputs of the memories.

25 Claims, 4 Drawing Sheets

APPARATUS FOR TREATING A SUBJECT WITH FOCUSED ULTRASOUND WAVES

BACKGROUND OF THE INVENTION

1. Field of the Invention

The present invention is directed to an apparatus for treating a subject with focused ultrasound waves, of the type having an ultrasound transducer composed of a plurality of ultrasound transducer elements and having a means for driving the ultrasound transducer that supplies electrical signals to the ultrasound transducer elements of the ultrasound transducer offset relative to one another in time corresponding to a desired position of the focus.

2. Description of the Prior Art

An apparatus of the above type is employed, for example, for treating pathological tissue changes. The pathological tissue is thereby heated by focused ultrasound waves emitted as therapeutic acoustic waves. Insofar as the occurring temperatures lie below 45° C., the metabolism is disturbed, with the result that, in the case of tumors, a retardation of the growth or even a regression of the tumor occurs. This type of treatment is known as local hyperthermia. When temperatures beyond 45° C. are reached, the cell protein coagulates, resulting in the necrotization of the tissue. This latter type of treatment is called thermotherapy.

The therapeutic acoustic waves are emitted as continuous sound or pulsed continuous sound.

A therapy apparatus of the type initially described can also be employed in the treatment of stone conditions (lithotripsy) and bone conditions (osteorestoration). The therapeutic acoustic waves are then emitted in the form of shock waves.

The possibility of being able to displace the focus of the acoustic waves is provided in order to enable a displacement of the focus within the subject to be treated without the ultrasound transducer and the subject under treatment having to be shifted relative to one another.

An apparatus of the type initially described is disclosed, for example, in German OS 43 02 538. In this apparatus, the displaceability of the focus is realized in that a delay element with adjustable delay time is allocated to each of the ultrasound transducer elements. The delay elements serve the purpose of delaying the signals supplied to the ultrasound transducer elements from a single oscillator for ultrasound generation or changing their phase position such that a desired focus position derives. The delay times of the delay elements are set with a control unit. Rather substantial technical outlay must thus be employed involving correspondingly high costs. Moreover, the complicated structure of the electronics involves a high space requirement.

Whereas a common oscillator supplies the signals required for ultrasound generation for all ultrasound transducer elements in the case of German OS 43 02 538, a drive circuit is allocated to each ultrasound transducer element in the case of an apparatus disclosed by U.S. Pat. No. 5,065,741, this drive circuit supplying the signals required for ultrasound generation to the respective ultrasound transducer element, whereby the points in time of the activation of the drive circuits are set by a computer—to which a memory is allocated—dependent on the interpretation of ultrasound images generated with an ultrasound locating means.

U.S. Pat. No. 5,158,071 also discloses an apparatus wherein a drive circuit is allocated to each ultrasound transducer element, this drive circuit supplying the signals for the respective ultrasound transducer element required for ultrasound generation, whereby the points in time of the activation of the drive circuits is set dependent on the respectively desired position of the focus.

German OS 30 48 527 discloses a diagnostic ultrasound applicator wherein a shared oscillator supplies the signals required for ultrasound generation for several groups of ultrasound transducer elements. The signals of the oscillator are thereby supplied to the individual groups via corresponding drive switches that are activated with a digital control element, for example an 8-bit D-register.

German OS 32 36 218 discloses a diagnostic ultrasound applicator wherein a demultiplexer/transmission unit supplies the signals required for the ultrasound generation for the ultrasound transducer elements. These signals are thereby supplied to the ultrasound transducer elements dependent on delay times stored in a memory.

SUMMARY OF THE INVENTION

An object of the present invention is to provide an apparatus of the type initially described but wherein the displacement of the focus of the acoustic waves is enabled in a technically simple and economic way.

The above object is achieved in accordance with the principles of the present invention in an apparatus for treating a subject with focused ultrasound waves having an ultrasound transducer composed of a number of ultrasound transducer elements, and means for driving the ultrasound transducer having a memory for each ultrasound transducer element in which a bit pattern is stored, corresponding to a desired position of the focus of the ultrasound waves during operation, and the means for driving also including a control unit which cyclically addresses the memories in parallel so that electrical signals, offset in time relative to each other according to the desired position of the focus, arise at the respective data outputs of the memories, and these electrical signals are respectively supplied to the ultrasound transducer elements for driving the overall ultrasound transducer.

In the case of the inventive apparatus, it is not the output signals of an oscillator or the like that are supplied to the ultrasound transducer elements as signals serving to generate ultrasound. Rather, the signals available at the data outputs of the memories are supplied to the ultrasound transducer elements as signals serving to generate ultrasound. For realization of the displacement of the focus in the inventive apparatus, thus, only a number of memories corresponding in number to the number of ultrasound transducer elements and one control unit addressing the memories are required. The memories and the components of the control unit are semiconductor components that can be economically obtained in the form of integrated circuits, so that a structure that is simpler, less expensive and that also saves installation space compared to a conventional apparatus is achieved. It is important in this context that, by contrast to the prior art, a setting of delay times need not occur since the phase position of the signals relative to one another is prescribed by the bit patterns.

According to an especially preferred embodiment of the invention, the apparatus contains write/read memories as memories into which the control unit writes the bit patterns corresponding to the desired position of the focus. In this way, it is possible to set different positions of the focus without having to replace the memories. In this context, it is provided in a modification of the invention that the control unit calculates the bit patterns corresponding to a desired position of the focus and writes them into the memories.

According to a preferred embodiment of the invention, however, it is provided that the control unit contains a data memory in which bit patterns are stored for different positions of the focus, and that the control unit writes the bit patterns corresponding to the respectively desired position of the focus into the memories. A simplified structure of the control unit derives in this way compared to the first-cited possibility since the calculation of the bit patterns can be eliminated. The number of positions of the focus with respect whereto bit patterns are stored is limited practically only by the capacity of the data memory. The different positions of the focus for which bit patterns are stored in the data memory are preferably arranged two-dimensionally or three-dimensionally matrix-like.

According to an embodiment of the invention, input means for a desired position of the focus are allocated to the control unit. The apparatus preferably includes a locating means with which an image of at least a region of the subject to be treated can be generated, whereby the input means are fashioned such that the respectively desired position of the focus is selectable in the generated image. For that case wherein the control unit is not fashioned such that it calculates the desired position of the corresponding bit pattern, it is then provided that the control unit writes that bit pattern stored in the data memory into the memories that lies closest to the desired position of the focus indicated with the input means.

Although X-ray locating means can be used, an ultrasound locating means is provided according to an embodiment of the invention. When the ultrasound locating means generates a tomogram at least of a region of the subject to be treated, in preferred embodiment of the invention the different positions of the focus stored in the data memory lie in a plane that is contained in the region of the subject to be treated that is imaged in the tomogram. It is assured in this way that the adjustable positions of the focus are in fact shown in the ultrasound image generated with the ultrasound locating means, so that the risk is slight that the focus is mistakenly brought into a position in which no treatment should in fact ensue.

It is especially advantageous when the ultrasound transducer provided for generating the focused ultrasound waves serving for treatment is also a component of the ultrasound locating means since it is then unnecessary to provide a separate ultrasound transducer for locating purposes. It is especially favorable in this context when the ultrasound transducer contains a linear arrangement (linear array) of ultrasound transducer elements since it is then possible to scan the subject to be treated in a purely electronic way in a linear scan in a known way for generating an ultrasound tomogram.

According to a modification of the invention, signal shaping means that convert the square-wave-like signals appearing at the data outputs of the memories into at least essentially sine-shaped signals are connected between the data outputs of the memories and the corresponding ultrasound transducer elements. Even though the electrical signals supplied to the ultrasound transducers are thus generated in a digital way, there is nonetheless the possibility of carrying out therapy with substantially sine-shaped ultrasound waves. Slight deviations of the electrical signals supplied to the ultrasound transducer elements from the sine shape are, moreover, without significance since distortions of the ultrasound waves on their path to the respective region to be treated occur anyway as a consequence of non-linear effects.

The signal shaping means can be realized in an especially simple and economic way when they contain LC networks.

It is clear from the above that a memory depth of 1 bit suffices for the memories allocated to the individual ultrasound transducer elements. The required memory length is dependent on the extent to which a displacement of the position of the focus is desired. According to one version of the invention, the memories respectively have a memory length of 16 bits each. The position of the focus can be displaced in the is way to a degree adequate for treatments in the urogenital region, particularly the prostate.

In order to assure an optimum function of the apparatus, the clock frequency with which the control unit addresses the memories must be equal to the frequency of the ultrasound waves multiplied by the memory length.

In order to also be able to generate ultrasound waves with higher intensity, driver stages connected between the data outputs of the memories and the corresponding ultrasound transducer elements are provided according to an embodiment of the invention. According to a preferred embodiment of the invention, the driver stages are connected to a power supply whose output voltage can be set with the control unit. There is thus the possibility of setting the amplitude of the electrical signals supplied to the ultrasound transducer elements and, thus, the amplitude of the generated ultrasound waves to the respective requirements.

For safety purposes, in order to assure for the sake of the safety of the patient that the amplitude of the ultrasound waves does not exceed the respectively desired degree, monitoring means are provided in a modification of the invention that measure the voltage and/or current at the outputs of the driver stages and/or at the outputs of the signal shaping means and/or at the output of the power supply and compare it to a corresponding reference value corresponding reference values.

Likewise for the safety of the patient, it is provided in an embodiment of the invention that the control unit writes bit patterns into the memories belonging to ultrasound transducer elements lying in the region of the edge of the ultrasound transducer that deviate such from the other memories that the waves emanating from the ultrasound transducer elements lying in the region of the edge of the ultrasound transducer exhibit a reduced intensity compared to the ultrasound waves emanating from the other ultrasound transducer elements. Interference phenomena that could lead to the formation of undesired subsidiary foci are avoided in this way. When the control unit writes bit patterns that respectively contain a sequence of bits placed in immediate succession into the memories belonging to ultrasound transducer elements not lying in the region of the edge of the ultrasound transducer, the reduced intensity in the region of the edge of the ultrasound transducer can be realized in a simple way in that bit patterns that contain a reduced number of successively set bits are written into the memories belonging to ultrasound transducer elements lying in the region of the edge of the ultrasound transducer.

DESCRIPTION OF THE DRAWINGS

FIGS. 4a, 4b, 4c and 4d show respective electrical signals for driving different ultrasound transducers (also shown schematically) of the inventive apparatus.

DESCRIPTION OF THE PREFERRED EMBODIMENTS

Figure 1:
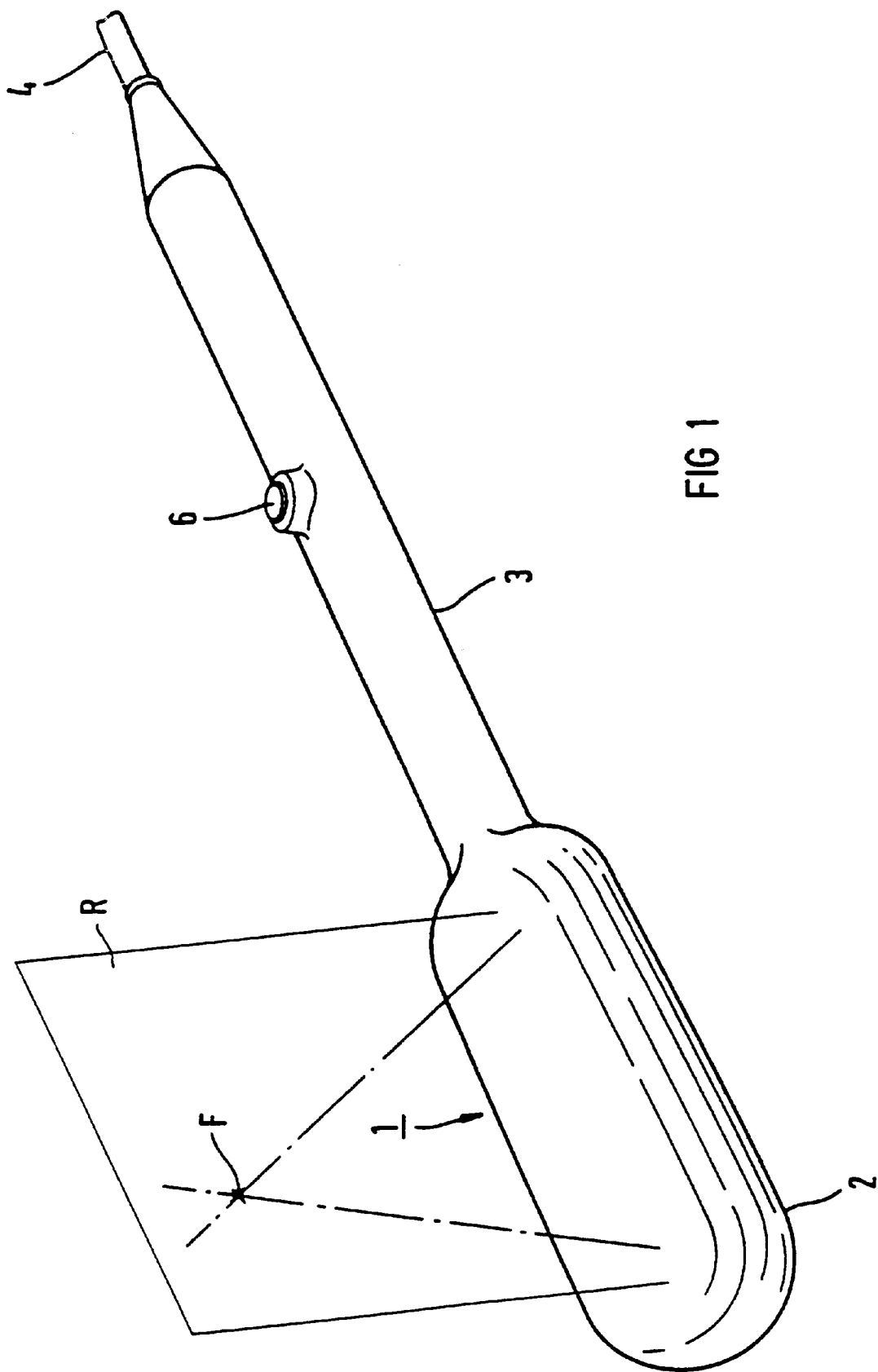
FIG. 1 is a perspective illustration of an ultrasound applicator, which contains the electroacoustic transducer, of an inventive therapy apparatus.

As a part of an inventive apparatus for treating benign prostate hyperplasia, FIG. 1 shows a handpiece referenced 1 that is provided for rectal application. The ultrasound applicator 1 has an approximately spoon-shaped design and has an approximately oval, flat application end 2 to which a handle 3 is attached. The application end, which has a thickness of about 15 mm, a width of about 30 mm and a length of about 60 mm, is provided for introduction into the rectum of the patient under treatment, from whom the handle 3 of the ultrasound applicator 1 then projects. The ultrasound applicator 1 is connected via a connecting cable 4 to the remaining elements of the apparatus shown in FIG. 3.

In its application end the ultrasound applicator 1 contains an ultrasound transducer 5 (shown in greater detail in FIG. 2) surrounded by an acoustic propagation medium, for example water, serving as an electroacoustic transducer. A key button 6 with which the attending physician can switch the apparatus from locating to therapy mode is attached in the region of the handle 3 of the ultrasound applicator 1, whereby the therapy mode is activated by pressing the key button 6, whereas the locating mode is activated when the key button 6 is not actuated.

In locating mode, the ultrasound transducer 5 generates diagnostic acoustic waves in the form of short ultrasound pulses whose length amounts to a few half cycles. In therapy mode, the ultrasound transducer 5 additionally generates focused therapeutic acoustic waves in the form of ultrasound waves. The therapeutic ultrasound waves can be continuous sound or pulsed continuous sound that is periodically briefly interrupted for the emission of the diagnostic ultrasound waves.

Figure 2:
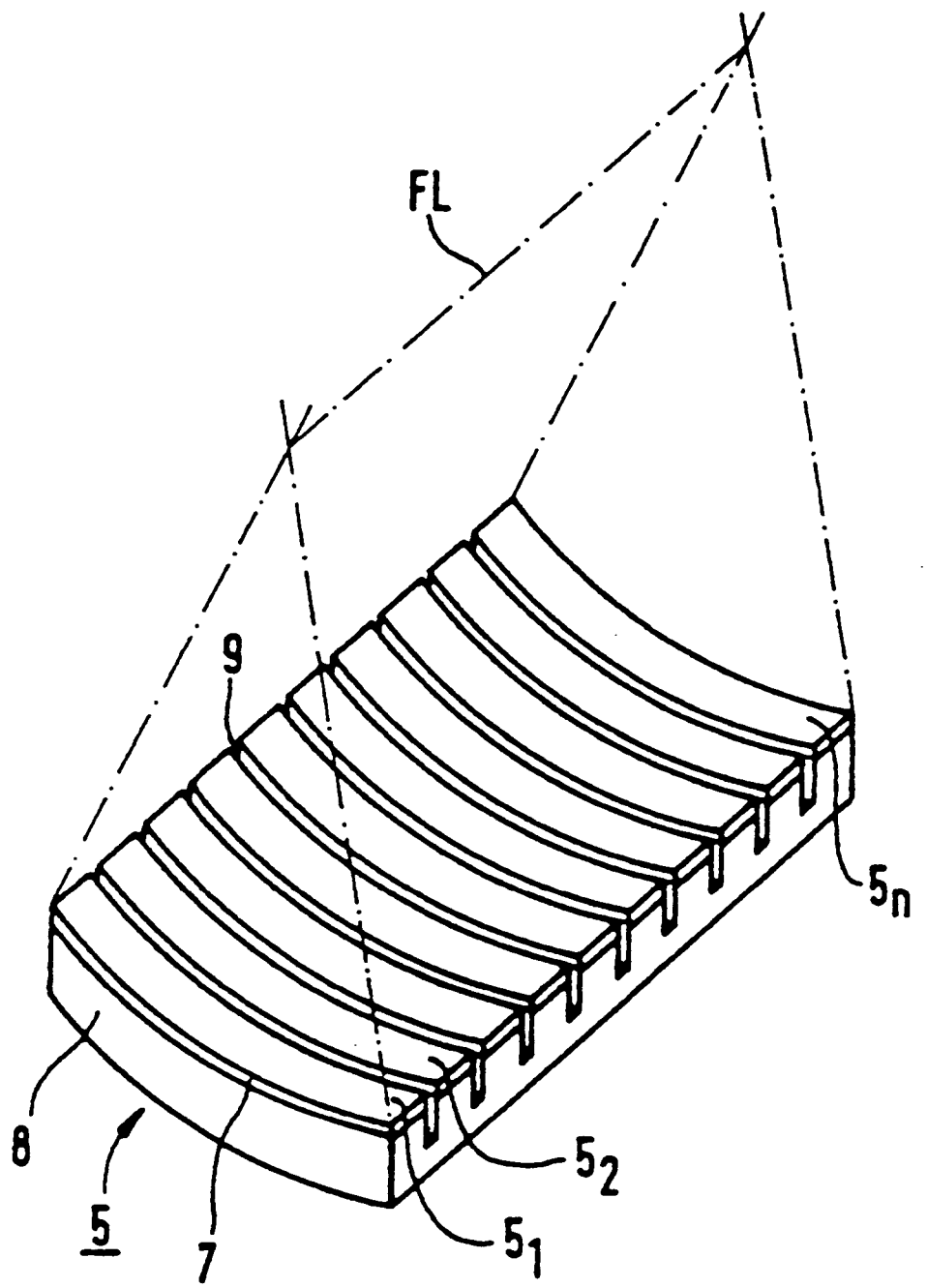
FIG. 2 is a perspective view of the ultrasound transducer contained in the applicator of FIG. 1.

According to FIG. 2, the ultrasound transducer 5 is constructed as a linear array, i.e. the ultrasound transducer 5 is divided into a number of ultrasound transducer elements $5_1$, $5_2$, etc., through $5_n$. The subdivision is executed such that it is fundamentally possible to individually drive each of the ultrasound transducer elements $5_1$ through $5_n$ to generate ultrasound waves by supplying a suitable electrical signal. In the way required in locating mode, it is likewise possible to separately take the electrical signals for the individual ultrasound transducer elements $5_1$ through $5_n$ arising due to the reception of parts of the diagnostic ultrasound waves reflected in the body of the life form under treatment.

For clarity, the ultrasound transducer shown in FIG. 2 is only divided into a few, namely ten ultrasound transducer elements. In practice, the ultrasound transducer 5 is divided, for example, into 128, 92 or 256 ultrasound transducer elements. The ultrasound transducer is constructed such in a known way that the actual piezoelectric material 7 is applied in the form of a layer with constant thickness on a carrying member 8 with suitable acoustic impedance that likewise has a constant thickness. The joining of the layer 7 of piezoelectric material to the carrying member 8 thereby ensues in a way not shown on the basis of a metallic layer whose thickness is small in relationship to that of the layer 7. That surface of the layer 7 facing away from the carrying member 8 is likewise provided with a thin metallic layer that is not shown. The metallic layers serve as electrodes for the electronic contacting of the ultrasound transducer elements $5_1$ through $5_n$.

In order to obtain ultrasound transducer elements $5_1$ through $5_n$ that can be driven independently of one another and whose output signals can be interrogated independently of one another, the piezoelectric layer 7 joined to the carrying member 8 is subdivided into the individual ultrasound transducer elements $5_1$ through $5_n$ by narrow incisions—one thereof is referenced 9 in FIG. 2—proceeding transversely relative to the longitudinal axis of the ultrasound transducer 5. In order to mechanically decouple the ultrasound transducer elements $5_1$ through $5_n$ from one another, the incisions 9 comprise a depth that is clearly greater than the thickness of the piezoelectric layer 7.

Given suitable drive of the individual ultrasound transducer elements $5_1$ through $5_n$, it is possible to focus the ultrasound waves emitted by the ultrasound transducer onto a focus zone and to displace the focus zone of the ultrasound waves. As is known, a focusing, or the implementation of a scan motion only in the direction of the longitudinal axis of the ultrasound transducer 5 or of the linear array is possible in this way. In order to also achieve a focusing transversely relative thereto, the ultrasound transducer 5 is cylindrically curved around an axis proceeding parallel to its longitudinal axis in the way indicated in FIG. 2 that is known from U.S. Pat. No. 4,159,462 in conjunction with diagnostic ultrasound transducers, so that, given simultaneous drive of all ultrasound transducer elements $5_1$ through $5_n$, a focusing of the ultrasound waves is achieved onto a line focus referenced FL in FIG. 2 that proceeds parallel to the longitudinal axis of the ultrasound transducer 5 or, respectively, of the linear array. Give drive of the ultrasound transducer 5 with a known diagnostic ultrasound apparatus 13 (see FIG. 3) in the fashion of a phased array, for example, a rectangular body slice of the life form under treatment can be scanned for locating purposes. A corresponding rectangle is indicated in FIG. 1 and referenced R. In the therapy mode, the center (referenced F in FIG. 1) of the respectively set focus zone can be displaced in the middle plane of the rectangular slice.

The drive of the ultrasound transducer elements $5_1$ through $5_n$ is described in greater detail below with reference to FIG. 3. Of the ultrasound transducer elements $5_1$ through $5_n$, the ultrasound transducer elements $5_1$ through $5_3$ and $5_{n1}$ through $5_n$ are shown by way of example. These are respectively connected to switches $10_1$ through $10_n$ via lines $4_1$ through $4_n$ of the connecting cable 4. The switches $10_1$ through $10_n$ are components of a control and image-generating electronics referenced 11 overall. The switches $10_1$ through $10_n$, which are preferably electronic switches, are actuated by a drive unit 12 so that all switches $10_1$ through $10_n$ respectively assume the same switch position. This is illustrated in FIG. 3 in that the switches $10_1$ through $10_n$ are connected to one another with a broken line.

Figure 3A:
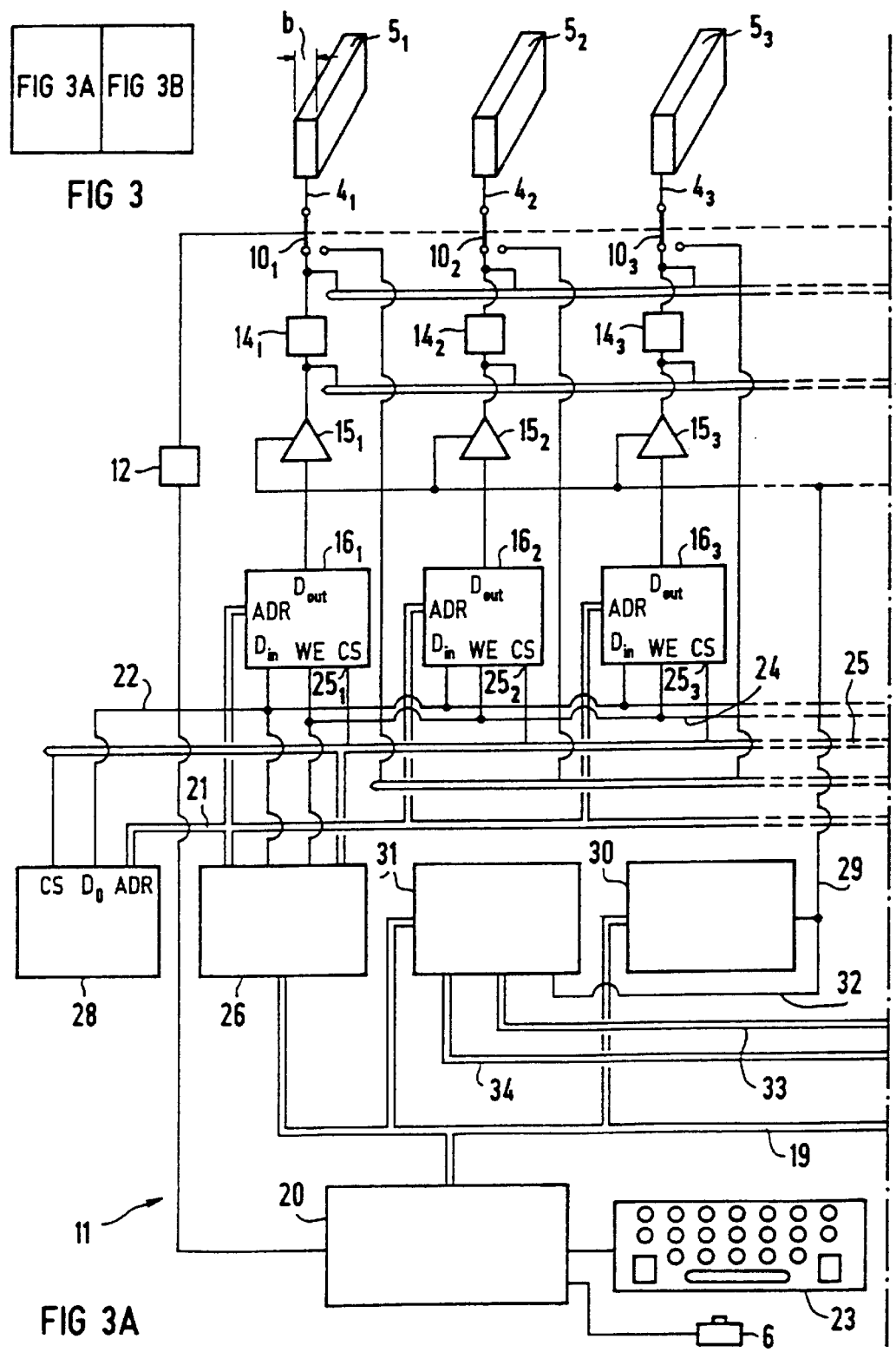
FIGS. 3A and 3B, in combination, form a block circuit diagram of the therapy apparatus of the invention.
Figure 3B:
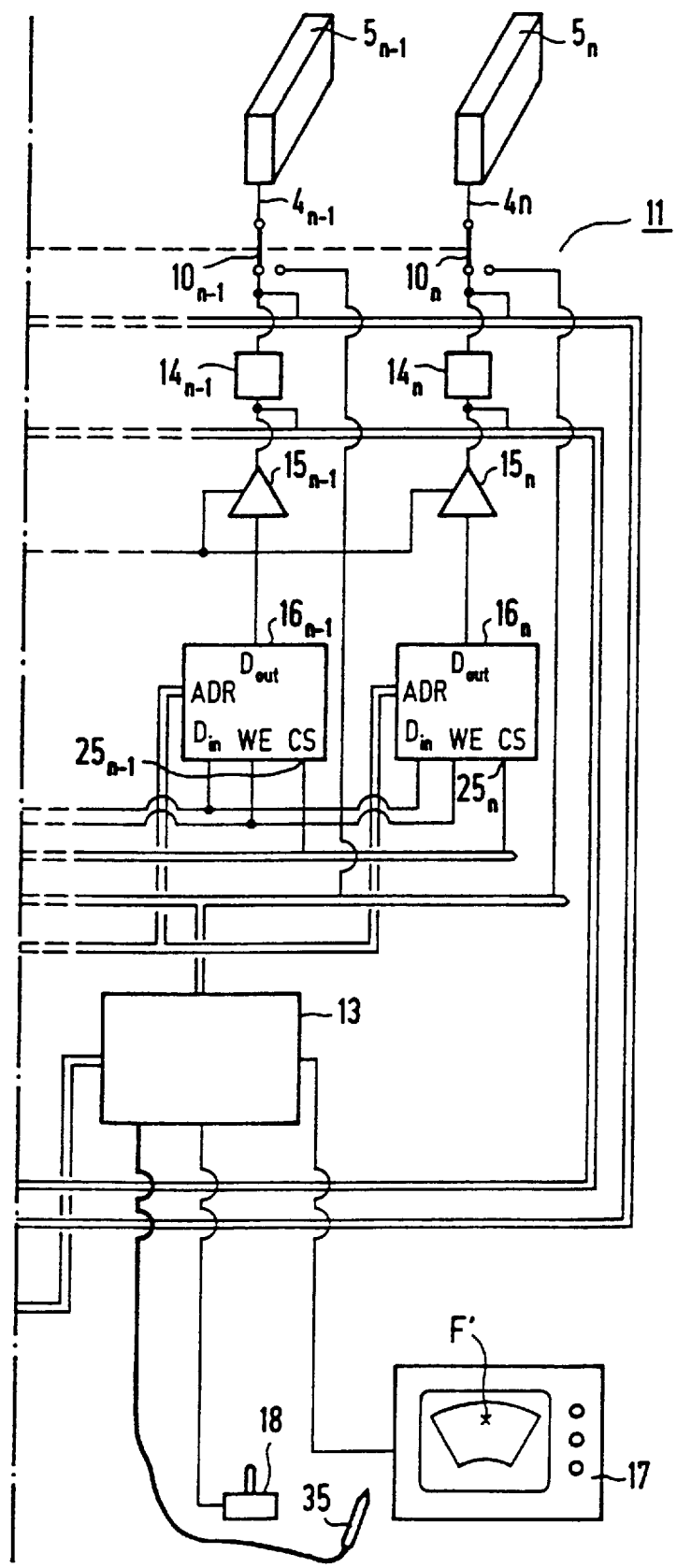

When the switches $10_1$ through $10_n$ assume their switch position that is not shown in FIG. 3, this corresponding to the locating mode, ultrasound transducer elements $5_1$ through $5_n$ are connected to a diagnostic ultrasound apparatus 13 that interacts with the ultrasound transducer 5 in a known way such that an image of the body slice of a patient under treatment that contains the longitudinal axis of the ultrasound transducer 5 and the line focus FL is generated and displayed on a monitor 17.

A joystick 18, with which it is possible to shift a mark F' mixed into the ultrasound image shown on the monitor 17, is connected to the ultrasound apparatus 13. Via a line bus 19, corresponding data or signals proceed to a control unit 20 that is a component of the control and image-generating electronic 11 that causes the therapeutic ultrasound waves emanating from the ultrasound transducer elements $5_1$ through $5_n$ in therapy mode to be focused onto a focus zone whose center F lies in the body of the life form under treatment at the location that corresponds to the location marked with the mark F' in the ultrasound image.

The therapeutic ultrasound waves are continuous sound or pulsed continuous sound. In therapy mode, which, as already mentioned, is activated by actuating the key button 6, the therapeutic ultrasound waves are periodically briefly interrupted in order to also update the ultrasound image during the therapy mode. To this end, a control unit belonging to the control and image-generating electronics 11 acts on the drive unit 12 and places the switches $10_1$ through $10_n$ into the position corresponding to a locating mode in the time required for generating an ultrasound image. Subsequently, the switches return into their switch position corresponding to the therapy mode until the preparation of the following ultrasound image. Whereas the ultrasound images are generated with a repetition rate of, for example 25 Hz in the locating mode, the repetition rate in the therapy mode lies, for example, at 0.1 through 1 Hz. Since the time required for generating an ultrasound scan is extremely short (clearly less than 1 millisecond), the pulse duration of the therapeutic ultrasound waves can be interrupted for negligibly short pauses in order to generate pulse-like diagnostic ultrasound waves. The pulse duration of the therapeutic ultrasound waves amounts to maximally about 1 through 10 seconds. Shorter pulse durations can be set.

When, by contrast, the switches $10_1$ through $10_n$ assume their switch position shown in FIG. 3, this corresponding to the therapy mode, the ultrasound transducer elements $5_1$ through $5_n$ of the ultrasound transducer 5 are connected to an arrangement for driving the ultrasound transducer 5. This contains a memory $16_1$ through $16_n$ for each of the ultrasound transducer elements $5_1$ through $5_n$, driver stages $15_1$ through $15_n$ following their data outputs $D_{out}$ and LC networks $14_1$ through $14_n$ forming signal shaping means connected between the latter and the ultrasound transducer elements $5_1$ through $5_n$. The memories are write/read memories (RAM). The control and image-generating electronics 11 is also a component of the arrangement for driving the ultrasound transducer 5, at least in part.

The address inputs ADR and the data inputs $D_{in}$ of the memories $16_1$ through $16_n$ are connected via an address bus 21 and a data line 22 to the control and image-generating electronics 11 that, moreover, contains a keyboard 23 serving for the operation of the apparatus.

As soon as a desired position of the focus zone is selected with the joystick 18, the control and image-generating electronics 11 switches the memories $16_1$ through $16_n$ into the write mode via a line leading to their WE (write enable) inputs and writes bit patterns corresponding to the desired position of the focus in the memories $16_1$ through $16_n$. Since the memories $16_1$ through $16_n$ are successively addressed during this write event and respectively comprise a memory depth of only 1 bit each, a single date line 22 that connects the data inputs of all memories $16_1$ through $16_n$ to the control and image-generating electronics 11 suffices. The described write event ensues sequentially in the sense that respectively only one of the memories $16_1$ through $16_n$ is enabled by the corresponding enable line $25_1$ through $25_n$ belonging to a line bus 25. The enable lines $25_1$ through $25_n$ are connected to the CS (chip select) inputs of the memories $16_1$ through $16_n$.

When the bit pattern corresponding to the desired position of the focus is written in each of the memories $16_1$ through $16_n$ and the apparatus is switched into the therapy mode by actuation of the key button 6, the control and image-generating electronics 11 switches all memories $16_1$ through $16_n$ into the read mode via the line 24 and addresses these in parallel and cyclically such that square-wave signals appear at the data output of the memories $16_1$ through $16_n$, these being offset in time relative to one another corresponding to the desired position of the focus. As used herein, parallel addressing means that respective the same memory cells are addressed in all memories $16_1$ through $16_n$ at a given point in time. As used herein, cyclical addressing means that all memory cells of the memories $16_1$ through $16_n$ are successively addressed ascending and descending, and this operation is always repeated, namely as long as the apparatus is switched into the therapy mode. As mentioned, brief interruptions are thereby provided from time to time for producing updated ultrasound images. It is self-evident that whether the cyclical addressing ensues ascending or descending must be taken into consideration in the bit patterns.

The square-wave signals appearing at the data outputs of the memories $16_1$ through $16_n$ have a frequency that corresponds to the quotient of the clock frequency with which the cyclical addressing of the memories $16_1$ through $16_n$ ensues and the memory length, 40 MHz or 16 bits in the case of the described exemplary embodiment. A frequency of the square-wave signals of 2.5 MHz thus derives in the case of the described exemplary embodiment.

After passing though the driver stages, the square-wave signals are converted by the LC networks into sine signals whose frequency corresponds to that of the square-wave signals.

The ultrasound transducer elements $5_1$ through $5_n$ of the ultrasound transducer are thus driven with sine signals in the fashion of a known phased array, these being phase-offset relative to one another such that the ultrasound waves generated with the ultrasound transducer 5 are focused onto a focus that assumes the respectively desired position.

The address signals and control signals required for writing the bit patterns into the memories $16_1$ through $16_n$ or for the readout of the bit patterns from the memories $16_1$ through $16_n$ are generated by an address and clock generator 26 to which the address bus 21, the data line 22, the line 24 and the line bus 25 are connected. The address and clock generator 26 is controlled by the control unit 20 to which it is connected via a line bus 19.

In a first operating mode that can be set with the keyboard 23, the control unit 20 calculates the bit patterns belonging to the position of the focus respectively selected with the joystick 18. The corresponding data then proceed via the line bus 19 to the control unit 20 and from the latter into the memories $16_1$ through $16_n$.

In a second operating mode that can likewise be selected with the keyboard 23, the address and clock generator 26 takes bit patterns belonging to a position of the focus selected with the joystick 18 from a data memory preferably implemented as a non-volatile memory, an EPROM 28 in the case of the described exemplary embodiment, and writes them into the memories $16_1$ through $16_n$. The EPROM 28 contains the bit patterns for a number of positions of the focus arranged matrix-like in a plane, whereby the plane is contained in the body slice that is imaged in the ultrasound image generated with the ultrasound apparatus 13.

The matrix-like arrangement of the positions of the focus with respect whereto bit patterns bit patterns are stored in the EPROM 28 is selected such taking the dimensions of the focus into consideration (in practice, a punctiform focus does not arise but instead a focus spatially three-dimensional zone) that a body region of the patient can be treated substantially gap-free. The −3 dB zone is advantageously assumed as the expanse of the focus, i.e. that region within which the acoustic pressure of the ultrasound waves amounts to at least 50% of the occurring peak acoustic pressure.

When a position of the focus for which no bit patterns are stored in the EPROM 28 is selected with the joystick 18, the control unit 20 and the address and clock generator 26 transfer those bit patterns from the EPROM 28 into the memories $16_1$ through $16_n$ that correspond to the position lying closest to the selected position of the focus with respect to which bit patterns are stored in the EPROM 28.

The driver stages $15_1$ through $15_n$ are connected via a delay line to a power supply 30 that belongs to the control and imaging electronics 11. The power supply 30 is in turn connected to the control unit 20 via the line bus 19 and is fashioned such that its output voltage is adjustable. In the case of the described exemplary embodiment, the output voltage of the power supply 30 is adjustable with input via the keyboard 23. The driver stages $15_1$ through $15_n$ are in turn fashioned such that the amplitude of the square-wave signals present at their outputs is proportional to the supply voltage supplied via the supply line 29. There is thus the possibility of matching the amplitude of the therapeutic ultrasound waves generated with the ultrasound transducer to the respective treatment case.

Since this is structurally the simplest, all driver stages $15_1$ through $15_n$ are supplied with the same voltage in the case of the described exemplary embodiment. In order to prevent the formation of secondary foci, however, it is expedient when the ultrasound transducer elements lying in the region of the edge of the ultrasound transducer 5, for example the ultrasound transducer elements $5_1$ and $5_2$ as well as $5_{n-1}$ and $5_n$, emit ultrasound waves with diminished intensity.

In the case of the described exemplary embodiment, this is achieved in that the control unit 20 writes bit patterns into the memories belonging to ultrasound transducer elements lying in the region of the edge of the ultrasound transducer 5, for example $16_1$ and $16_2$ or $16_{n-1}$ and $16_n$, deviating from the other memories such that the corresponding ultrasound waves exhibit a reducing intensity.

FIG. 4 shows the bit patterns stored in the corresponding memories for some ultrasound transducer elements (from top to bottom: ultrasound transducer elements $5_1$ and $5_n$, ultrasound transducer elements $5_2$ and $5_{n-1}$, an ultrasound transducer element lying between middle and edge, a middle ultrasound transducer element) and the square-wave signals respectively thereunder that appear at the data outputs of the corresponding memory. As can be seen from FIG. 4, four successive bits are set in each of the cases of the ultrasound transducer elements distanced from the edge of the ultrasound transducer, whereas a reduced number of successive bits are set in the case of the ultrasound transducer elements at the edge. This achieves the result that, after conversion of the square-wave signals appearing at the outputs of the memories into sine-shaped signals, the sine signals belonging to the ultrasound transducer elements at the edge exhibit a reduced amplitude.

In order, for the safety of the patient, to preclude therapeutic ultrasound waves with too high an amplitude from being generated in therapy mode, a monitoring circuit 31 is provided. The monitoring circuit 31 via a schematically indicated test line 32 and likewise schematically indicated test line busses 33 and 34, measures the voltages present at the output of the power supply 30, the outputs of the driver circuits $15_1$ through $15_n$ and the outputs of the LC networks $14_1$ through $14_n$, as well as the currents occurring at these points, and compares them to appropriate thresholds. When one of the thresholds is exceeded, the monitoring circuit 31 informs the control unit 20 of this, being connected thereto via the line bus 19. The control unit 20 then lowers the supply voltage delivered by the power supply 30 to such an extent that a transgression of the threshold is no longer present.

For implementation of a treatment, the application end 2 of the ultrasound applicator 1 is introduced into the rectum of the patient. The actuation of the key button 6 is omitted for the moment. The ultrasound applicator 1 is then aligned such that the subject to be treated appears in the ultrasound image. With the joystick 18, the attending physician then sets the mark F to the zone to be treated. The physician then presses the key button 6 at the handle 3, causing a switch is made to therapy mode. Therapeutic ultrasound waves are then emitted, their effective zone assuming such a position in the subject to be treated that its center F is located at the place corresponding to the set position of the mark F'. Since a brief switch is constantly made into the locating mode in the above-described way during the therapy, the user is lent the impression of a real-time presentation and is constantly informed about the therapeutic result. Since the ultrasound transducer 5 is located in the ultrasound applicator 1, it is easily possible to displace the effective zone during the therapy since the position of the effective zone can be seen at any time on the basis of the mark mixed into the ultrasound image.

The therapy mode is then exited by releasing the key button 6. The apparatus then automatically continues to run in locating mode.

In another operating mode, there is the possibility of tracing a region to be treated with a light pen 35 indicated in FIG. 3 (or with a mark displaceable via the joystick 18) in the ultrasound image displayed on the monitor. The position of the focus is then displaced little by little by the control unit, which causes the respectively required bit patterns to be written into the memories $16_1$ through $16_1$, until the entire body region lying within the region marked with the light pen is treated with therapeutic acoustic waves. In this operating mode, it is expedient for means for fixing the ultrasonic applicator 1, for example a stand (not shown), are provided in order to minimize the risk of dislocations of the handpiece 1 relative to the body of the patient.

The frequency of the therapeutic ultrasound waves generated in therapy mode is preferably lower than the frequency of the diagnostic ultrasound waves that are output in locating mode. A high spatial resolution is thus advantageously obtained in the production of the ultrasound images, so that it is possible to locate to zone to be treated with high precision and to position the effective zone in the zone to be treated with enhanced precision. At the same time, it is assured that the therapeutic ultrasound waves are not unnecessarily attenuated.

Particularly when the ultrasound apparatus 13 provide the possibility of implementing not only linear scans but sector scans as well for the locating, it is expedient to select the width b of the ultrasound transducer elements $5_1$ through $5_n$ such that it is less than half the wavelength of the diagnostic ultrasound waves in the respective acoustic propagation medium, i.e. the propagation medium contained in the ultrasound applicator 1, or in the body tissue of the life form under treatment. It is thereby assured that the emission of the diagnostic ultrasound waves ensues undirected, this being a pre-condition for being able to scan a sector-shaped body slice of a life form under treatment in the described way.

Since this can lead to a number of ultrasound transducer elements that is too high in and of itself for the generation of the therapeutic ultrasound waves because of their longer wavelength, it can be provided that a number of ultrasound transducer elements be combined to form an ultrasound transducer element group for generating the therapeutic ultrasound waves. In the case of the described exemplary embodiment, this can be accomplished by writing the same bit pattern into the respective memories for all of the transducer elements belonging to an ultrasound transducer element group.

The number of ultrasound transducer elements belonging to an ultrasound transducer element group would then correspond to the quotient of the number of ultrasound transducer elements present overall and the memory length. It is self-evident that it must be assured that the overall width of an ultrasound transducer element group is smaller than half the wavelength of the therapeutic ultrasound waves in the acoustic propagation medium. The emission of the therapeutic ultrasound waves then ensues undirected, this being a pre-condition for being able to displace the effective zone in the described way.

Each ultrasound transducer element can be a single ultrasound transducer element in the strict sense. In the way disclosed in German OS 43 02 538, however, there is also the possibility of forming an ultrasound transducer element with a number of ultrasound transducer (sub-) elements connected parallel, these being in communication with a shared memory via a shared LC network and a shared driver stage. For example, 256 ultrasound transducer (sub-) elements can thus be combined into 16 ultrasound transducer elements, each of which contains 16 ultrasound transducer (sub-) elements. An LC network, a driver stage and a memory is then required for each of the ultrasound transducer elements formed of respectively 16 ultrasound transducer (sub-) elements. It is also true here that the number of ultrasound transducer (sub-) elements combined in an ultrasound transducer element must be selected such that the width of the resultant ultrasound transducer element is less than half the wavelength of the therapeutic ultrasound waves in the respective acoustic propagation medium.

The frequency of the therapeutic ultrasound waves and that of the diagnostic ultrasound waves are selected such in the way disclosed in German OS 43 02 538 that the ultrasound transducer elements $5_1$ through $5_n$ of the ultrasound transducer 5 work under resonant conditions (fundamental wavelength/harmonic) in the therapy as well as in locating mode.

The aforementioned German OS 43 02 538 is also referenced with respect to the width b and the thickness of the ultrasound transducer elements $5_1$ through $5_n$.

In the case of the described exemplary embodiment, there is the possibility of optionally taking the bit patterns to be written into the memories $16_1$ through $16_n$ from the EPROM 28 or of having the calculated by the control unit 20. However, other embodiments are also possible that make use of only the one or other of these possibilities.

The ultrasound transducer 5 in the described exemplary embodiment is a one-dimensional array of ultrasound transducer elements $5_1$ through $5_n$. Accordingly, the focus of the generated ultrasound waves can be two-dimensionally displaced, namely in a plane. There is also the possibility of employing a two-dimensional array of ultrasound transducer elements as ultrasound transducer. The focus of the generated therapeutic ultrasound waves can then be three-dimensionally displaced. A two-dimensional array of ultrasound transducer elements can, for example, include a number of ultrasound transducer elements arranged matrix-like in a plane. There is also the possibility of providing drive means for the displacement of the ultrasound transducer 5 (for example, within the handpiece 1) relative to the body of the patient in order to enable a displacement of the focus.

The above-described exemplary embodiment is directed to an apparatus that is rectally applied, i.e. that is employed partially invasively and that is provided for the treatment of benign prostate hyperplasia. However, other apparatus that are extra-corporeally, i.e. non-invasively applied and/or that serve for the treatment of other conditions can also be fashioned in accordance with the principles of the present invention.

In the case of the described exemplary embodiment, LC networks and driver stages are connected between the data outputs of the memories and the ultrasound transducer elements. These can be omitted in favor of a direct connection of the data outputs of the memories and the ultrasound transducer elements when the data outputs of the memories can supply an adequately high current. The signals available at the data outputs of the memories are then directly supplied to the ultrasound transducer elements for ultrasound generation.

As used herein a phased array means an arrangement of a number of ultrasound transducer elements that can be electronically focused by time-delayed drive. A linear array means a linear arrangement of a number of ultrasound transducer elements. As used herein a scan means, for example, a linear scan or a sector scan with an ultrasound beam.

Although modifications and changes may be suggested by those skilled in the art, it is the intention of the inventor to embody within the patent warranted hereon all changes and modifications as reasonably and properly come within the scope of his contribution to the art.

We claim as our invention:

1. An apparatus for treating a subject with focused acoustic waves, comprising:

an ultrasound transducer composed of a plurality of ultrasound transducer elements for emitting therapeutic ultrasound waves converging at a focus;

a plurality of memories respectively connected to said plurality of ultrasound transducer elements, each memory, during operation, storing a bit pattern therein corresponding to a position of said focus of said ultrasound waves, and each memory having an output;

control means for cyclically addressing said memories in parallel for producing electrical signals at the respective outputs of said memories, said electrical signals being offset in time relative to each other according to said position of said focus; and drive means, supplied with said electrical signals, for driving said ultrasound transducer elements according to said electrical signals for emitting said ultrasound waves focused at said position of said focus.

2. An apparatus as claimed in claim 1 wherein each of said memories comprises a write/read memory, and wherein said control means comprises means for writing, into each memory, said bit pattern corresponding to said position of said focus.

3. An apparatus as claimed in claim 2 wherein said control means comprises a data memory in which a bit pattern for each memory is stored for a plurality of different positions of said focus, and wherein said control means comprises means for retrieving a set of said bit patterns for one of said plurality of positions and for writing the respective bit patterns in said set into the respective memories.

4. An apparatus as claimed in claim 3 wherein said data memory comprises means for storing said bit patterns for different positions of said focus in a two-dimensional matrix.

5. An apparatus as claimed in claim 1 wherein said control means comprises means for calculating, for each memory, said bit pattern corresponding to said position of said focus.

6. An apparatus as claimed in claim 3 wherein said data memory comprises means for storing said bit patterns for different positions of said focus in a three-dimensional matrix.

7. An apparatus as claimed in claim 2 wherein said control means comprises input means for entering a selected position of said focus.

8. An apparatus as claimed in claim 1 further comprising locating means for producing an image of at least a region of a subject to be treated with said ultrasound waves, said locating means including input means for producing an identifier in said image for a selected position of said focus.

9. An apparatus as claimed in claim 8 wherein said locating means comprises an ultrasound locating means.

10. An apparatus as claimed in claim 9 wherein said ultrasound transducer is a component of said ultrasound locating means, said ultrasound locating means comprising means for operating said ultrasound transducer to emit diagnostic ultrasound.

11. An apparatus as claimed in claim 10 wherein said ultrasound transducer comprises a linear array of said ultrasound transducer elements.

12. An apparatus as claimed in claim 11 wherein said means for operating said ultrasound transducer to emit diagnostic ultrasound comprises means for operating said ultrasound transducer for conducting a linear scan for generating an ultrasound tomogram.

13. An apparatus as claimed in claim 9 wherein said control unit comprises a data memory in which a plurality of sets of bit patterns for the respective memories are stored respectively for a plurality of different positions of said focus, wherein said control means includes means for writing bit patterns in a set of bit patterns corresponding to a selected one of said positions of said focus into the respective memories, and wherein said ultrasound locating means comprises means for generating a tomogram in a plane of said region with said different positions of said focus for which datasets are stored in said data memory and which lie in said plane, are identified in said image in said tomogram.

14. An apparatus as claimed in claim 1 wherein said electrical signals comprise square wave signals, and wherein said drive means includes signal shaping means, connected between each of said outputs of said memories and each of said ultrasound transducer elements, for converting said square wave signals into signals having substantially a sinusoidal shape.

15. An apparatus as claimed in claim 14 wherein said signal shaping means includes a plurality of LC networks.

16. An apparatus as claimed in claim 14 wherein said signal shaping means includes a plurality of signal shaping stages respectively connected between said outputs of said memories and said ultrasound transducer elements, each signal shaping stage having an output at which a voltage and a current are present, and said apparatus further comprising monitoring means for monitoring an output parameter, comprising at least one said voltage and said current, at the output of each signal shaping stage, and for comparing said monitored parameter to a reference value.

17. An apparatus as claimed in claim 14 wherein each of said memories has a memory depth of one bit.

18. An apparatus as claimed in claim 17 wherein each of said memories has a memory length of sixteen bits.

19. An apparatus as claimed in claim 1 wherein said therapeutic ultrasound waves have a frequency and wherein each of said memories has a memory length, and wherein said control means comprises means for addressing said memories with a clock frequency equal to said frequency of said therapeutic ultrasound wave multiplied by said memory length.

20. An apparatus as claimed in claim 1 wherein said drive means comprises a plurality of driver stages respectively connected between the outputs of said memories and said ultrasound transducer elements.

21. An apparatus as claimed in claim 20 further comprising a power supply unit having an output voltage, said power supply unit being connected to each of said driver stages, and wherein said control means comprises means for setting said output voltage of said power supply unit.

22. An apparatus as claimed in claim 21 further comprising monitoring means for monitoring said output voltage of said power supply unit and for comparing said output voltage to a reference value.

23. An apparatus as claimed in claim 20 wherein each of said driver stages has an output at which a voltage and a current are present, and said apparatus further comprising monitoring means for monitoring an output parameter, comprised of at least one of said voltage or current, at the output of each said driver stages and for comparing said monitored parameter to a reference value.

24. An apparatus as claimed in claim 1 wherein said ultrasound transducer has an edge, and wherein said ultrasound transducer elements include ultrasound transducer elements disposed at said edge of said ultrasound transducer, and wherein said control means comprises means for writing a bit pattern into the respective memories for said ultrasound transducer elements disposed at said edge for causing said ultrasound transducer elements disposed at said edge to emit said therapeutic ultrasound waves at an intensity which is less than an intensity of the therapeutic ultrasound waves emitted by a remainder of said ultrasound transducer elements.

25. An apparatus as claimed in claim 24 wherein said control means comprises means for writing a bit pattern into the respective memories for said remainder of said ultrasound transducer elements containing a sequence of a first number of immediately successive set bits, and for writing bit patterns into the respective memories for said ultrasound transducer elements at edge containing a sequence of a second number of immediately successive set bits, said second number being less than said first number.

* * * * *